United States Patent [19]

Zoller et al.

[11] Patent Number: 4,837,225
[45] Date of Patent: Jun. 6, 1989

[54] 2,5-DIMETHYLPYRROLE DERIVATIVES, THEIR PREPARATION AND THEIR USE

[75] Inventors: Gerhard Zoller, Schöneck; Rudi Beyerle, Frankfurt am Main; Ursula Schindler, Mörfelden-Walldorf; Rolf-Eberhard Nitz, Frankfurt am Main; Piero Martorana, Bad Homburg, all of Fed. Rep. of Germany

[73] Assignee: Cassell Aktiengesellschaft, Frankfurt, Fed. Rep. of Germany

[21] Appl. No.: 888,050

[22] Filed: Jul. 17, 1986

[30] Foreign Application Priority Data

Aug. 2, 1985 [DE] Fed. Rep. of Germany ....... 3527791

[51] Int. Cl.$^4$ .................. C07D 207/239; A61K 31/40
[52] U.S. Cl. .................................... 514/427; 540/544; 548/198; 548/214; 548/518; 548/558; 548/561; 514/428; 514/423
[58] Field of Search ................ 540/544; 548/198, 214, 548/518, 558, 561

[56] References Cited

U.S. PATENT DOCUMENTS 3,702,331  11/1972  Tike .................................. 548/558

OTHER PUBLICATIONS

Desimoni and Minoli in "Tetrahedron", vol. 26, pp. 1393–1400 (1970).

Primary Examiner—Robert T. Bond

Attorney, Agent, or Firm—Perman & Green

[57] ABSTRACT

2,5-Dimethylpyrrole derivatives of the formula I

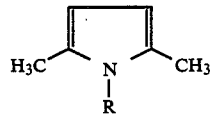
(I)

in which R denotes alkyl which is substituted by —NH$_2$, acylamino of the formula

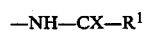

or by an optionally substituted heterocycle having 1 hetero member; or denotes an optionally substituted heterocycle having 1 member, and X and R$^1$ have the meanings given and their pharmacologically acceptable acid addition salts, their preparation by reaction of amines of the formula II

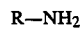
(II)

with acetonylacetone or by acylating N-aminoalkyl-2,5-dimethylpyrroles, and their use as pharmaceutical active compounds.

4 Claims, No Drawings

2,5-DIMETHYLPYRROLE DERIVATIVES, THEIR PREPARATION AND THEIR USE

The present invention relates to 2,5-dimethylpyrrole derivatives of the formula I

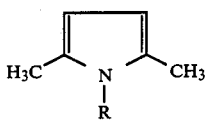

in which R denotes alkyl which is substituted by -NH$_2$, acylamino of the formula

or by an optionally substituted aliphatic or aromatic 5- to 7-membered heterocycle having 1 hetero member; or denotes an optionally substituted aliphatic or aromatic 5- to 7-membered heterocycle having 1 hetero member, X represents an oxygen or sulphur atom, and R$^1$ denotes hydrogen; optionally substituted alkyl; cycloalkyl having 5 to 7 C atoms, optionally substituted phenyl; an optionally substituted aliphatic or aromatic 5- to 7-membered heterocycle having 1 or 2 hetero members; an amino group (—NH$_2$) or optionally substituted phenylamino, and to their pharmacologically acceptable acid addition salts, to their preparation by reaction of amines of the formula II
R—NH$_2$ (II)

with acetonylacetone or, where appropriate, acylation of N-amino-alkyl-2,3-dimethylpyrroles, and to their use a pharmaceutical active compounds.

In particular, the invention relates to 2,5-dimehtylpyrrole derivatives of the formula I

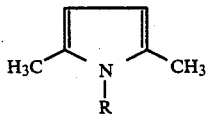

in which R denotes alkyl which has 1 to 3 C atoms and is substituted by —NH$_2$, acylamino of the formlua

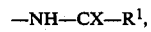

or by an optionally substituted aliphatic or aromatic 5- to 7-membered heterocycle having 1 hetero member; or denotes an optionally substituted aliphatic or aromatic 5- to 7-membered heterocycle having 1 hetero member, X represents an oxygen or sulphur atom, and R$^1$ denotes hydrogen; alkyl which has 1 to 5, preferably 1 or 2, C atoms and is optionally substituted by -NH$_2$, monoalkylamino having 1 to 4, preferably 1 to 2, C atoms, dialkylamino having a total of 2 to 6, preferably 2 to 4, C atoms, an N-pyrrolidinyl, N-piperidinyl, N-morpholinyl or N-thiomorpholinyl radical, or by a 1-piperazinyl radical which is substituted in the 4-position optionally by alkyl having 1 to 4 C atoms, phenyl, toluyl, chlorophenyl or methoxyphenyl or ethoxyphenyl, or by alkoxy having 1 to 4, preferably 1 or 2, C atoms or by optionally substituted phenoxy; cycloalkyl having 5 to 7 C atoms; optionally substituted phenyl; an optionally substituted aliphatic or aromatic 5- to 7-membered heterocycle having 1 or 2 hetero members; an amino group (-NH$_2$) or phenylamino whose phenyl nucleus is optionally substituted by chlorine, alkyl having 1 or 2 C atoms, alkoxy having 1 or 2 C atoms, carboxyl or alkoxycarbonyl having 1 or 2 C atoms in the alkoxy group.

If, in an acylamino group of the formula —NH—CX—R$^1$ representing R, the symbol X represents a sulphur atom, then R$^1$ preferably denotes an amino group (—NH$_2$) of phenylamino whose phenyl nucleus is optionally substituted by chlorine, alkyl having 1 or 2 C atoms, alkoxy having 1 or 2 C atoms, carbocyl or alkoxycarbonyl having 1 or 2 C atoms in the alkoxy group.

The optionally substituted aliphatic or aromatic 5- to 7-membered heterocycles representing R or R$^1$ or being present as a substituent of an alkyl radical representing R preferably contain

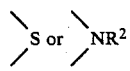

as the hetero member. Where the heterocycle has 2 hetero members these can be identical or different. A nitrogen-containing heterocycle can also be bonded via the hetero N atom; in addition to the first nitrogen atom establishing the bond, it can also contain any one of the abovementioned hetero members. Examples of heterocyclic radicals of this type which are bonded via a hetero N atom are, for example, the N-pyrrolidino radical or the N-thiomorpholino radical.

Aromatic heterocyclic radicals are those which, because of conjugation of double bonds, where appropriate with electron pairs, can form resonating structures within the ring, such as, for example, the thienyl radical or the pyrazolyl radical. Aliphatic heterocyclic radicals contain only isolated or zero double bonds, such as, for example, the pyrrolidino radical, the piperidino radical, the morpholin radical or the perhydrothiazepino radical. Those of the heterocycles containing two hetero members which are preferred are those which have at least one nitrogen-containing hetero member.

Examples of heterocycles from which are derived heterocyclic radicals representing R or R$^1$ or being bonded to an alkyl group representing R are: thiophene, di- or tetrahydrothiophene, pyrrole, pyrroline, pyrrolidine, pyridine, dihydropyridine, piperidine, pyran, perhydropyran, oxepine, theipine, azepine, perhydrooxepine, perhydrothiepine, perhydroazepine, imidazole, imidazoline, imidazolidine, oxazole, oxazoline, oxazolidine, thiazole, thiazoline, thiazolidine, pyrimidine, pyridazine, pyrazine, piperazine, morpholine, thiomorpholine, diazepine, oxazepine, thiazepine and perhydrodiazepine, -oxazepine and -thiazepine.

Particularly preferred heterocyclic radicals are derived from pyrrole, pyrrolidine, thiazole, thiazolidine and perhydrothiazepine.

In the hetero members of the formula

R$^2$ represents hydrogen, alkyl having 1 to 4, preferably 1 or 2, C atoms or alkoxycarbonyl having 1 to 4 C atoms in the alkoxy group.

The heterocyclic radicals can also carry on one of the ring carbon atoms a substituent such as, for example, a carboxyl group, alkoxycarbonyl having 1 to 4, preferably 1 or 2, C atoms in the alkoxy group or, preferably, an alkyl group having 1 to 4 preferably 1 or 2, C atoms.

Aliphatic heterocyclic radicals, especially those which are derived from nitrogen heterocycles, can also have on a ring carbon atom, preferably on a ring carbon atom adjacent to the nitrogen-containing hetero member, a keto group, a double-bonded oxygen atom.

A phenyl radical representing $R^1$, and a phenoxy radical bonded as substituent to an alkyl group representing $R^1$ can, in turn, carry up to three substituents in the nucleus namely an amino group, monoalkylamino having 1 to 4, preferably 1 or 2, C atoms, dialkylamino having a total of 2 to 6, preferably 2 to 4, C atoms, alkanoylamino having 1 to 6, preferably 1 or 2, C atoms, alkyl having 1 to 4, preferably 1 or 2, C atoms, alkoxy having 1 to 4, preferably 1 or 2, C atoms, halogen, preferably fluorine, chlorine or bromine, expecially fluorine or chlorine, hydroxyl, nitro, cyano, carboxyl or alkoxycarbonyl having 1 to 4, preferably 1 or 2, C atoms in the alkoxy group. Suitable as an optional second substituent of the nucleus are: one of the alkyl or alkoxy groups defined above or one of the abovementioned halogens and, as third substituent, one of the alkyl or alkoxy groups above.

A single substituent may be located in the 2-, 3- or 4-position of the phenyl or phenoxy nucleus. In the case of double substitution the 2,4-, the 3,4- and the 3,5-position of the possible positions are preferred. Suitable for triple substitution are the positions 2,3,4 and 3,4,5 and 2,4,6.

Preferred substituents for the said phenyl nuclei are chlorine, alkyl and alkoxy having 1 or 2 C atoms, in particular methyl or methoxy, carboxyl and alkoxycarbonyl having 1 or 2 C atoms in the alkoxy group. Furthermore, in addition to the unsubstituted nuclei, preference is given to the monosubstituted and disubstituted ones which carry an alkoxy radical as second substituent.

The same stipulations, restricted to the substituents possible in this case, apply to the number and position of the substituents in the phenyl nucleus of an optionally substituted phenylamino group representing $R^1$ as apply to the phenyl and phenoxy radicals described above.

In a toluyl, chlorophenyl or alkoxyphenyl radical bonded to the piperazino group it is possible for the substituents to be located in the 2-, 3- or 4-position, preferably in the 2- or 4-position, relative to the piperazino radical.

Specific especially preferred radicals R are alkyl radicals having from 1 to 3 C atoms which are substituted by one of the following substituents: formylamino, acetylamino, propionylamino, isopropionylamino, butyrylamino, 4-chlorophenoxyacetylamino, (2-oxo-1-pyrrolidinyl)acetylamino, N,N-dimethylaminoacetylamino, L-thiazolidin-4-yl-carbonylamino, 4-chlorobenzoylamino, 5-oxoperhydro-1,4-thiazepin-3-aminocarbonylamino, 4-chlorophenylaminocarbonylamino, 1-acetyl-L-pyrrolidin-2-ylcarbonylamino, 1-ethyl-2-pyrolidinyl, 2-oxo-1-pyrrolidinyl and 2-oxoperhydro-3-azepinyl.

Examples of further valuable substituents of an alkyl radical representing R and having 1 to 3 C atoms are: the amino group, 3,4-dimethoxybenzoylamino, 2-(4-(2-methoxyphenyl)piperazinyl)acetylamino, isobutyrylamino, 3-tert.-butoxycarbonyl-4-thiazolidinylcarbonylamino, 4-ethoxycarbonylphenylaminocarbonylamino, 4-ethoxycarbonylphenylaminothiocarbonylamino, 4-carboxyphenylaminocarbonylamino, 4-carboxyphenylaminothiocarbonylamino, 4-thiazolidinyl, 2-oxo-1-pyrrolidinyl and 2-methyl-4-pyrrolyl.

An example of a valuable heterocycle representing R is the 5-oxoperhydro-1,4-thiazepin-3-yl radical.

Particularly preferred dimethylpyrrole derivatives according to the invention are those which have two or more of the abovementioned preferred features.

The preparation of the compounds of the general formula I according to the invention,

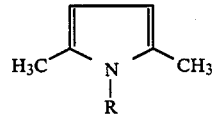

(I)

in which R has the abovementioned meanings, and of their physiologically tolerated acid addition salts, can be carried out in a manner such that acetonylacetone is reacted with primary amines of the formula $H_2N$-R or their acid addition salts, in a suitable solvent at temperatures from 20° to 150° C., preferably below 100° C., in particular at 40° to 20° C., and, where R is an alkyl radical which has 1 to 3 atoms and is substituted by a radical of the formula $-NH-CX-R^1$, if desired the acyl radical $-CX-R^1$ is eliminated by hydrolysis in a manner known per se.

If desried, for example when a particularly low-boiling solvent is used, it is possible for the ring-closure reaction also be be carried out under pressure above the boiling point of the reaction mixture. However, the process is preferably carried out below or at the boiling point of the solvent used.

Examples of suitable solvents are alcohols, in particular those having 1 to 6 C atoms, such as, for example, methanol, ethanol; i- and n-propanol, i-, sec- and tert-butanol, n-, i-, sec-, tert-pentanol, n-hexanol, cyclopentanol cyclohexanol, ethers, especially those having 2 to 8 C atoms in the molecule, such as, for example, diethyl ether, methyl ethyl ether, di-n-propyl ether, diisopropyl ether, methyl n-butyl ether, ethyl propyl ether, dibutyl ether, tetrahydrofuran, 1,4-dioxane, 1,2-dimethoxyethane, bis-β-methoxyethyl ether; polyethers such as, for example, polyethylene glycols having a molecular weight up to about 600; oligoethylene glycol dimethyl ethers such as, for example, pentaglyme; aliphatic carboxylic acids, especially formic and acetic acid; glycols and partially etherified glycols such as, for example, ethylene glycol, propylene glycol, trimethylene glycol, ethylene glycol monomethyl ether, ethylene glycol monoethyl ether, diethylene glycol monoethyl ether; aliphatic hydrocarbons such as, for example, low- and high-boiling petroleum ethers; aromatic hdrocarbons such as, for example, benzene, toluene, o-, m- and p-xylene; halogenated aliphatic or aromatic hydrocarbons such as, for example, methylene chloide, chloroform, carbon tetrachloride, chlorobenzene, dichlorobenzene; nitriles such as, for example, acetonitrile; amides such as, for example, dimethylformamide, N-methylpyrrolidone; hexamethylphosphoric acid triamide; sulphoxides such as, for example, dimethyl sulphoxide; water. It is also possible to use mixtures of various solvents.

In the preparation of the compounds of the formlua I the starting components are normally used in approximately equimolar amounts. The amine of formula II can also be used in the form of an acid addition salt. The working up of the mixtures is carried out by customary methods. The reaction can, where appropriate, also be carried out in the presence of a base or a mixture of bases. Examples of suitable bases are tertiary aliphatic amines such as, for example, triethylamine, tri-n-propylamine and tri-isopropylamine, also pyridine, as well as alkali metal carbonates and bicarbonates.

The elimination which may be desired, of the acyl radical from compounds of the formula I, according to the invention, in which R is an alkyl radical substituted by the group —NH—CX—R$^1$, 

results in the corresponding compounds in which the alkyl radical representing R is substituted by a primary amino group, The elimination is carried out by hydrolysis in a manner known per se. For this purpose, the compounds are treated with water or an organic medium containing water in the presence of molar amounts of a base. The duration of the treatment depends on the temperature selected. It is possible to work at room temperature or, in order to increase the rate of hydrolysis, at elevated temperatures, expediently up to the reflux temperature of the liquid hydrolysis medium.

The nature of the base which is to be added is, in principle, of no consequence. These reagents should merely bring about an adequately high OH$^-$ concentration and allow straight-forward working up of the mixtures. The choice of these agents can thus take place in a known manner.

On the other hand, it is also possible for the preparation of the compounds of the formula I, according to the invention, in which R is an alkyl radical which has 1 to 3 C atoms and is substituted by an acylamino group of the formula —NH—CO—R$^1$, to acylate aminoalkyl-pyrroles of the formula III

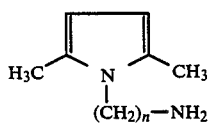

(III)

in which n is a number from 1 to 3, with reactive carboxylic acid derivatives derived from carboxylic acids of the formula R$^1$—COOH, in which R$^1$ has the above-mentioned meaning, with alkali metal cyanate or thiocyanate or with isocyanates or isothiocyanates of the formula R$^3$—NCX, 

in which X is oxygen or sulphur and R$^3$ denotes optionally substituted phenyl, preferably phenyl which is optionally substituted, expecially in the manner detailed above, by chlorine, alkyl having 1 or 2 C atoms, alkoxy having 1 or 2 C atoms, carboxyl or alkoxycarbonyl having 1 or 2 C atoms in the alkoxy group.

Suitable reactive carboxylic acid derivatives are carboxylic esters, carboxylic anhydrides, carboxylic chlorides or carboxylic acids which are activated in situ such as, for example, using dicyclohexylcarbodiimide (Houben-Weyl 8, 522), oxalyl chloride (British Patent No. 2139-225), N,N-carbonyldiimidazole (J. Med. Chem. 1982, 620; Synthesis 9182, 833; Chem. Pharm. Bull. 32, 5044 (1984)); N,N'-carbonyldiazoles (Bull. Chem. Soc. Jap. 57, 3597 (1984)); di(2-pyridyl) carbonates (Tetrahedron Lett. 25, 4943 (1983)); chloroformic esters (Tetrahedron Lett. 24, 3365 (1983)); diphosphorus tetraiodide (Chem. Lett. 1983, 449); dialkyl disulphite (Indian J. Chem. 21, 259 (1982)); methylethylphosphinic anhydride, or using other reactive agents.

When isocyanates or isothiocyanates of the formulae R$^3$—NCO or R$^3$—NCS are used as acylating agents, the 2,3-dimethyl-pyrrole derivatives according to the invention which are obtained are those in which R is an alkyl radical substituted by the groups —HN—CO—NH—R$^3$ or —NH—CS—NH—R$^3$. Reaction of the amines of the formlua II with alkali metal cyanates or thiocyanates provides compounds, according to the invention, in which R is an alkyl radical substituted by the groups —NH—CO—NH$_2$ or —NH—CS—NH$_2$.

The reactions are expediently carried out in the liquid phase, it being advantageous for an inert solvent to be present.

Moreover, if pure enantiomers of the carboxylic acid derivatives of amines are used it is possible for the compounds of the formula I, according to the invention, to be obtained as the pure enantiometers of the compounds.

Where the 2,5-dimethylpyrrole derivatives of the formula I contain basic radicals they form acid addition salts with inorganic or organic acids. Suitable for the formation of acid addition salts of this type are inorganic or organic acids. Examples of suitable acids are: hydrogen chloride, hydrogen bromide, naphthalenedisulphonic acids, especially naphthalene-1,5-disulphonic acid, phosphoric, nitric, sulphuric, oxalic, lactic, tartaric, acetic, salicylic, benzoic, formic, propionic, pivalic, diethylacetic, malonic, succinic, pimelic, fumaric, maleic, malic, sulphamic, phenylpropionic, gluconic, ascorbic, nicotinic, isonicotinic, methanesulphonic, p-toluenesulphonic, citric or adipic acid. Pharmacologically acceptable acid addition salts are preferred. The acid addition salts are prepared as customary by mixing the components, expediently in a suitable solvent or diluent. It is possible in the synthesis of the compounds of the formula I for the acid addition salts to be produced first during the course of working up. It is possible to obtain the free compounds of the general formula I, if desired, from the acid addition salts in a manner known per se, for example by dissolution or suspension in water and by making alkaline, for example using sodium hydroxide solution, followed by isolation.

The compounds of the formula I, according to the invention, and their pharmacologically acceptable acid addition salts have valuable pharmacological properties. They have central actions, for example they exhibit encephalotropic and sychotropic effects and are used for the treatment of disorder of brain function, such as cerebral insufficiency, cerebral aging processes, and deterioration in memory as also occurs in Alzheim's disease or multi-infarct dementia or where the faculty of learning is diminished. Surprisingly, they are considerably superior to the compounds which are hiterto known to act in the same direction. They show an excellent activity in a variety of test types, such as, for example, in the prolongation of the survival time during sodium nitrite hypoxia by the method of Gibsen and Blass (J.

Neurochemistry 27, 37 (1976)), in the improvement in the nitrogen-induced hypoxia tolerance, where experimental animals are premedicated with the investigated products and then ventilated with pure nitrogen, and the prolongation of the time between the start of ventilation and electrical neutrality of the electroencephalogram and the mortality are measured.

The products according to the invention also have very high activity in tests which are aimed directly at measuring the faculties of learning and memory, such as, for example, the well-known "avoidance" tests.

Testing in the said tests and a number of other tests such as, for example, the 65 -butyrolactone test shows that the compounds according to the invention surprisingly exhibit, at low doses where the toxicity is low, a particularly favourable profile of action which does not exit in this form for known products.

The compounds of the formula I and their physiologically tolerated salts thus represent an enrichment of pharmacy.

The compounds of the formula I and their physiologically tolerated salts thus represent an enrichment of pharmacy.

The compounds of the formula I and the abovementioned compounds and their pharmacologically acceptable acid addition salts can be administered as medicaments alone, mixed with one another or in the form of pharmaceutical compositions which permit enternal or parenteral administration and which contain as active constituents an effective dose of at least one compound of the formula I or an abovementioned compound or an acid addition salt thereof, in addition to customary pharmaceutically acceptable vehicles and additivies. The compositions normally contain about 0.5 to 90% by weight of the therapeutically active compound.

The medicaments can be administered orally, for example in the form of pills, tablets, lacquers, coated tablets, granules, hard and soft gelatin capsules, solutions, syrups, emulsions or suspensions, or aerosol mixtures. However, administration can also be effected, for example in the form of suppositories, or parenterally, for example in the form of injection solutions, or percutaneously, for example in the form of ointments or tinctures.

The pharmaceutrical products are prepared in a manner known per se, use being made of pharmaceutically inert inorganic or organic vehicles. For the preparation of pills, tablets, coated tablets and hard gelatin capsules, it is possible to make use of, for example, lactose, maize starch or derivatives thereof, talc, stearic acid or its salts, etc. Examples of vehicles for soft gelatin capsules and suppositories are fats, waxes, semi-solid and liquid polyols, natural or hardened oils etc. Examples of suitable vehicles for the preparation of solutions and syrups are water, sucrose, invert sugar, glucose, polyols etc. Examples of suitable vehicles for the preparation of injection solutions are water, alcohols, glycerol, polyols, vegetable oils etc.

In addition to the active compounds and vehicles, the pharmaceutical products can also contain additives such as, for example, fillers, extenders, disintegrants, binders, lubricants, wetting agents, stabilizers, emulsifiers, preservatives, sweeteners, colorants, flavourings or aromatizing substances, thickening agents, diluents, buffer substances, as well as solvents or solubilizers or agents to achieve a depot effect, and salts to modify the osmotic pressure, coating agents or antioxidants. They can also contain two or more compounds of the formula I or their pharmacologically acceptable acid addition salts together with one or more other therapeutrically active compounds.

Examples of other therapeutically active substances of this type are agents promoting blood flow, such as dihydroergocristine, nicergoline, buphenine, buphenine, nicotinic acid and its esters, pyridylcarbinol, bencyclan, cinnarizine, naftidrofuryl, raubasine and vincamine; positive inotropic compounds, such as digoxin, acetyldigoxin, metildigoxin and lanatosides; coronary dilators such as carbocromen, dipyridamol, nifedipine and perhexiline, antianginal compounds such as isosorbide dinitrate, isosorbide mononitrate, glycerol nitrate, molsidomine and verapamil, $\beta$-blockers such as propranolol, oxprenolol, artenolol, metoprolol and penbutolol. Furthermore, the compounds can be combined with other substances having psychotropic activity, such as, for example, piracetam, or ZNS-active substances such as pirlindole, sulpiride etc.

The dosage can vary within wide limits and should be adjusted to the individual circumstances in each particular case. In general, on oral administration a daily dose of about 0.1 to 1 mg/kg, preferably 0.3 to 0.5 mg/kg, of body weight is appropriate to achieve effective results, and on intravenous administration the daily dose is generally about 0.01 to 0.3 mg/kg, preferably 0.05 to 0.1 mg/kg, of body weight. The daily dose is normally, especially when relatively large amounts are administered, divided into several, for example 2, 3 or 4, administrations of part thereof. Where appropriate, it may be necessary, depending on the individual behaviour, to increase or reduce the daily dose indicated. Pharmaceutircal products normally contain 0.1 to 50 mg, preferably 0.5 to 10 mg, of active compound of the formula I or of the said compounds or of a pharmacologically acceptable salt per dose.

EXAMPLE 1

2,5-Dimethyl-1-(2-(2-oxo-1-pyrrolidinyl)ethyl)pyrrole 5.7 g (0.05 mmol) of acetonylacetone and 6.4 g (0.05 mmol) of 1-(2-aminoethyl)-2-pyrrolidinone are heated under reflux in 70 ml of methanol for 2 h. The reaction mixture is then concentrated and, after the concentration, the crude reaction product is then precipitated by addition of petroleum ether. The crude product is recrystallized from diethyl ether. Yield: 3.2 g (31% of theory), Melting point: 66°–68° C. Elemental analysis: $C_{12}H_{18}N_2O$ (206.29) calculated: C 69.9 H 8.8 N 13.6 0 7.8 found: C 69.4 H 8.7 N 13.7 0 8.11

EXAMPLE 2

2,5-Dimethyl-1-(s-oxoperhydro-3-azepinyl)pyrrole 21 g (0.1 mol) of a 60% strength aqueous solution of 3-amino-$\epsilon$-caprolactam are subjected to azeotropic removal of water with 200 ml of chloroform, and 11.4 g (0.1 mol) of acetonylacetone in 150 ml of ethylene glycol monomethyl ether are added, and the mixture is stirred at 80° C. for 2 h. After concentration of the reaction mixture, it is stirred with ether and the resulting precipitate is filtered off with suction. Yield: 16.4 g (79% of theory), Melting point: 150°–152° C. Elemental analysis: $C_{12}H_{18}N_2O$ (206.29) calculated: C 69.9 H 8.8 N 13.6 0 7.8 found: C 69.3 H 8.4 N 13.5 ) 8.3

EXAMPLE 3

2,5-Dimethyl-1-(1-ethyl-2-pyrolidinyl)methyl)pyrrole 11.4 g (0.1 mol) of acetonylacetone and 12.8 g (0.1 mol) of 1-ethyl-2-aminomethylpyrrolildine are heated under reflux in 120 ml of isopropanol for 1 h. The reaction mixture is concentrated, and fractional distillation in vacuo is carried out. Yield: 13.2 g (64% of theory), Boiling point: 73° C./0.4 mbar Elemental analysis: $C_{13}H_{22}N_2$ (206.34) calculated: C 75.7 H 10.7 N 13.6 found: C 75.9 H 10.3 N 13.1

EXAMPLE 4

2,5-Dimethyl-1-(5-methyl-2-pyrrolyl)methyl)pyrrole 11.4 g (0.1 mol) of acetonylacetone and 11 g (0.1 mol) of 5-methyl-2-aminomethylpyrrole are heated under reflux in 100 ml of 1,2-dimethoxyethane for 1 h. The reaction mixture is concentrated, and fractional distillation in vacuo is carried out. Yield: 5.8 g (31% of theory), Boiling point: 90° C./0.133 mbar Elemental analysis: $C_{12}H_{16}N_2$ (188.8) calculated: C 76.6 H 8.7 N 14.9 found: C 75.9 H 9.0 N 14.3

EXAMPLE 5

2,5-Dimethyl-1-(2-acetylaminoethyl)pyrrole 171.2 g (1.5 mol) of acetonylacetone and 153.2 g (1.5 mol) of 1-acetylethylenediamine are heated under reflux in 1.8 l of ethanol for 3 h. The reaction mixture is concentrated, and the residue is recrystallized from toluene. Yield: 259.3 g (96% of theory), Melting point: 106°-107° C. Elemental analysis: $C_{10}H_{16}N_2O$ (180.25) calculated: C 66.6 H 8.9 N 15.5 0 8.9 found: C 66.8 H 8.8 N 15.6 0 8.9

EXAMPLE 6

1-(2-Aminoethyl)-2,5-dimethylpyrrole 251.1 g (1.39 mol) of 2,5-dimethyl-1-(2-acetylaminoethyl)-pyrrole, prepared as in Example 5, and 390.8 g (6.97 mol) of potassium hydroxide are heated reflux in 2.8 l of ethanol and 180 ml of water under an atmosphere of nitrogen for 4 h. After the mixture has been concentrated, the aqueous phase is extracted with methylene chloride, and the extract is fractionally distilled. Yield: 150.2 g (78% of theory), Boiling point: 70° C./0.267 mbar

EXAMPLE 7

N-(2-(2,5-Dimethyl-1-pyrrolyl)ehtyl)-N'-(4-ethoxycarbonylphenyl)-urea 5.5 g (0.05 mol) of 1,-(2-aminoethyl)-2,5-dimethylpyrrole are dissolved in 20 ml of methylene chloride. 7.6 g (0.04 mol) of 4-ethoxycarbonylphenyl isocyanate in 20 ml of methylene chloride are added dropwise to this solution at room temperature. The precipitate which separates out is filtered off with suction and recrystallized from ethanol. Yield: 7.3 g (55% of theory), Melting point: 181°-182° C. Elemental analysis: $C_{18}H_{23}N_3O_3$ (329.40) calculated: C 65.6 H 7.0 N 12.8 O 14.6 found: C 65.0 H 7.2 N 12.9 O 14.8

EXAMPLE 8

N-(2-(2,5-Dimethyl-1-pyrrolyl)ethyl)-N'-(4-carboxyphenyl)urea 3.3 g (0.01 mol) of N-(2-(2,5-dimethyl-1-pyrrolyl)ethyl)-N'-(4-ethoxycarbonylphenyl)urea, prepared as in Example 7, are stirred with 12 ml of methanol and 10 ml of 1 N sodium hydroxide solution at room temperature for 1 h and then acidified with dilute hydrochloric acid. The precipitated product is filtered off with suction and dried. Yield: 1.5 g (50% of theory), Melting point: 248°-250° C. Elemental analysis: $C_{16}H_{19}N_3O_3$ (301.35) calculated: C 63.8 H 6.4 N 13.9 O 15.9 found: C 63.4 H 6.2 N 13.9 O 16.3

Example 9

N-(2-(2,5-Dimethyl-1-pyrrolyl)ethyl)-N'-(4-ethoxycarbonylphenyl)-thiourea 8.3 g (0.04 mol) of 4-ethoxy carbonylphenyl isothiocyanate in 20 ml of ethylene glycol dimethyl ether are added dropwise at room temperature to 5.5 g (0.04 mol) of 1-(2-aminoethyl)-2,5-dimethylpyrrole in 20 ml of ethylene glycol dimethyl ether. The precipitated product is filtered off with suction and recrystallized from methanol. Yield: 5.1 g (37% of theory) Melting point: 155°-156° C. Elemental analysis: $C_{18}H_{23}N_3O_2S$ (345.47) calculated: C 62.6 H 6.7 N 12.2 0. 9.3 S 9.3 found: C 62.0 H 6.7 N 11.6 0 10.0 S 9.2

EXAMPLE 10

N-(2-(2,5-Dimethyl-1-pyrrolyl)ethyl)-N'-(4-carboxyphenyl)thiourea 2.8 g (0.008 mol) of N-(2-(2,5-dimethyl-1-pyrrolyl)ethyl)-N'-(4-ethoxycarbonylphenyl)thiourea, prepared as in Example 9, are stirred with 10 ml of 1 N sodium hydroxide solution at room temperature for 5 h and under reflux for 15 min. After cooling, the mixture is filtered, and the filtrate is acidified and the product is filtered off with suction. yield: 1.9 g (75% of theory), Melting point: 174°-175° C. Elemental analysis: $C_{16}H_{19}N_3O_2S$ (317.41) calculated C 60.5 H 6.0 N 13.2 0 10.1 S 10.1 found: C 59.9 H 5.9 N 13.6 0 10.7 S 9.9

EXAMPLE 11

N-(2-(2,5-Dimethyl-1-pyrrolyl)ethyl)-N'-(4-chlorophenyl)urea 7.7 g (0.05 mol) of 4-chlorophenyl isocyanate, dissolved in 10 ml of tetrahydrofura, are added dropwise, over the coruse of 30 minutes, to 6.9 g (0.05 mol) of 1-(2-aminoethyl)-2,5-dimethylpyrrole, dissolved in 10 ml of tetrahydrofuran, a 20° C. The mixture is then left to stir at 20° C. for 60 minutes. After addition of diethyl ether to the reaction mixture the product crystallizes out, and is filtered off with suction and recrystallized from isopropanol. Yield: 8.4 g (58% of theory), Melting point: 175°-177° C. Elemental analysis: $C_{15}H_{18}ClN_3O$ (291.83) calculated: C 61.7 H 6.2 CL 12.2 N 14.4 0 5.5 found: C 61.0 H 6.5 Cl 12.5 N 14.6 0 5.8

EXAMPLE 12

2-(2,5-Dimethyl-1-pyrolyl)ethylurea 6.9 g (0.05 mol) of 1-(2-aminoethyl)2,5-dimethylpyrrole are dissolved in 8 ml of water. While cooling, 5 ml of concentrated hydrochloric acid are slowly added dropwise, and then 4.9 g (0.05 mol) of potassium cyanate, dissolved in 30 ml of water, are added dropwise. The precipitated solid is filtered off with suction and recrystallized from toluene/ethyl acetate. Yield: 3.8 g (42% of theory), Melting point: 139°-141° C. Elemental analysis: $C_9H_{15}N_3O$ (181.24) calculated: C 59.6 H 8.3 N 23.2 0 8.8 found: C 59.2 H 8.2 N 22.8 0 9.1

EXAMPLE 13

N-(2-(2,5-Dimethyl-1-pyrrolyl)ethyl)-4-chlorophenoxyacetamide 9.3 g (0.05 mol) of 4-chlorophenoxyacetic acid, 6.9 g (0.05 mol) of 1-(2-aminoethyl)-2,5-dimethylpyrrole and 35 ml of triethylamine are dissolved in 50 ml of dimethylformamide. At −5° to 0° C., 20 ml of methylethylphosphinic anhydride are added dropwise, and the mixture is then stirred at room temperature for 3 h. The reaction mixture is poured into ice-cold aqueous sodium bicarbonate solution, and the mixture is extracted with methylene chloride and the extract is concentrated. The residue is chromatographed over a 20 cm silica gel column using a 1:1 methylene chloride/ethyl acetate mixture as the mobile phase, and the product is crystallized using ligroin. Yield: 10.5 g (69% of theory), Melting point: 75°-77° C. Elemental analysis: $C_{16}H_{19}ClN_2O_2$ (306.80) calculated: C 62.6 H 6.2 CL 11.6 N 9.1 0 10.4 found: C 62.7 H 6.4 CL 11.7 N 9.2 0 10.4

EXAMPLE 14

N-(2-(2,5-Dimethyl-1-pyrrolyl)ethyl)-(2-oxo-1-pyrrolidinyl)acetamide 14.3 g (0.1 mol) of (2-oxo-1-pyrrolidinyl)acetic acid and 16.2 g (0.1 mol) of N,N'-carbonyldiimidazole are heated under reflux in 70 ml of tetrahydrofuran for 15 min. After cooling, 13.8 g (0.1 mol) of 1-(2-aminoethyl)-2,5-dimethylpyrrole in 70 ml of tetrahydrofuran are added dropwise. After the reactionmixture has been stirred at room temperature for 6 h, it is concentrated, acifified with dilute acetic acid and extracted with methylene chloride. The methylene chloride extract is concentrated, and the residue is triturated with ether, filtered off with suction and recrystallized from dibuyl ether. Yield: 9.0 g (34% of theory), Melting point: 109°-111° C. Elemental analysis: $C_{14}H_{21}N_3O_2$ (263.34) calculated: C 63.9 H 8.0 N 16.0 O 12.2 found: C 63.8 H 8.0 N 15.9 O 12.2

EXAMPLE 15 n-(2-(2,5-Dimethyl-1-pyrrolyl)ethyl)-1-acetyltetrahydropyrrole-2-carboxamide 6.3 g (0.04 mol) of 1-acetyl-L-proline and 6.5 g (0.04 mol) of carbonyldiimidazole in 20 ml of DMF are stirred at 60° C. for 10 min. After addition of 5.5 g (0.04 mol) of 1-(2-aminoethyl)-2,5-dimethylpyrrole to the mixture it is stirred at room temperature for 3 h, then concentrated, worked up as in Example 14, and the product is recrystallized from toluene. Yield: 5.7 g (51% of theory), Melting point: 131°-133° C. Elemental analysis: $C_{15}H_{23}N_3O_2$ (277.37) calculated: C 65.0 H 8.3 N 15.2 0 11.5 found: C 65.2 H 7.9 N 15.3 0 11.4

EXAMPLE 16

N-(2-(2,5-Dimethyl-1-pyrrolyl)ethyl)-3,4-dimethoxybenzamide 9.1 g (0.05 mol) of 3,4-dimethoxybenzoic acid and 8.2 g (0.05 mol) of carbonyldiimidazole in 50 ml of dioxane are stirred at 60° C. for 15 min. After addition of 6.2 g (0.045 mol) of 1-(2-aminoethyl)2,5-dimethylpyrrole in 20 ml of dioxane to the mixture it is stirred at room temperature for 20 h, concentrated, and aqueous sodium bicarbonate solution is added and the mixture is extracted with methylene chloride. The extract is chromatographed over an alumina column, and the product is crystallized using ethyl acetate/ether/ligroin. Yield: 6.9 g (46% of theory), Melting point: 82°-84° C. Elemental analysis: $C_{17}H_{22}N_2O_3$ (302.37) calculated: C 67.5 H 7.3 N 9.3 O 15.9 found: C 67.3 H 7.2 N 8.8 O 16.6

EXAMPLE 17

N-(2-(2,5-Dimethyl-1-pyrrolyl)ethyl-5-oxoperhydro-1,4-thiazepine-3-carboxamide 3.5 g (0.02 mol) of 5-oxoperhydro-1,4-thiazepine-3-carboxylic acid and 2.8 g (0.02 mol) of 1-(2-aminoethyl)-2,5-dimethylpyrrole are dissolved in 10 ml of dimethylformamide. After addition of 4.2 g (0.02 mol) of dicyclohexylcarbodiimide, dissolved in 10 ml of methylene chloride, to the mixture at 0° C., it is stirred at room temperature for 24 h, then water is added and the mixture is filtered with suction. The filtrate is extracted with methylene chloride, and the extract is chromatographed over a silica gel column using ethyl acetate as the mobile phase. Yield: 1.2 g (20% of theory), Melting point: 181°-183° C. Elemental analysis: $C_{14}H_{21}N_3O_2S$ (295.41) calculated: C 56.9 H 7.2 N 14.2 0 10.8 S 10.9 found: C 57.4 H 6.9 N 13.8 0 11.2 S 10.8

EXAMPLE 18

N-(2-(2,5-Dimethyl-1-pyrrolyl)ethyl-n-butyramide 6.4 g (0.04 mol) of butyric anhydride, dissolved in 20 ml of toluene, are added dropwise to 5.5 g (0.04 mol) of 1-(2-amino-ethyl)-2,3-dimethylpyrrole, dissolved in 20 ml of toluene, at room temperature. The mixture is then stirred for 5 h, concentrated, and aqueous sodium bicarbonate solution is added and the mixture is extracted with methylene chloride. The extract is concentrated and the resulting residue is recrystallized from dibutyl ether. Yield: 4.8 g (58% of theory), Melting point: 66°-68° C. Elemental analysis: $C_{12}H_{20}N_2O$ (208.31) calculated: C 69.2 H 9.7 N 13.4 O 7.7 found: C 68.7 H 9.3 N 13.5 O 8.6

EXAMPLE 19

N-2-(2,5-Dimethyl-1-pyrrolyl)ethyl-4-chlorobenzamide 7.0 g (0.04 mol) of 4-cholorobenzoyl chloride, dissolved in 20 ml of methylene chloride, are added dropwise to 5.5 g (0.04 mol) of 1-(2-aminoethyl)-2,5-dimethylpyrrole, dissolved in 30 ml of pyridine, at 0° C. The mixture is stirred at 0° C. for 1 h and at room temperature for 4 h, the excess acid chloride is hydrolysed by the addition of water, and the reaction product is extracted with methylene chloride, and the extract is concentrated. The resulting crude product can be recrystallized from Ligoin. Yield: 5.4 g (49% of thory), Melting point: 104°-105° C. Elemental analysis: $C_{15}H_{17}ClN_2O$ (276.82) calculated: C 65.1 H 6.2 Cl 12.8 N 10.1 O 5.8 found: C 65.4 H 6.1 Cl 12.5 N 10.1 O 5.9

EXAMPLE 20

N-(2-(2,5-Dimethyl-1-pyrrolyl)ethyl)-(N,N-dimethylamino)acetamide 5.2 g (0.05 mol) of N,N-dimethylaminoacetic acid and 8.1 g (0.05 mol) of carbonyldiimidazole in 20 ml of ethylene glycol dimethyl ether are stirred at 70° C. for 15 min. After addition of 5.5 g (0.04 mol) of 1-(2-aminoethyl)-2,5-dimethylpyrrole, dissolved in 20 ml of ethylene glycol dimethyl ether, to the mixture it is stirred at room temperature for 5 h, then concentrated, water is added, and the mixture is extracted first when acid and then when alkaline. The product contained in the extract from the mixture which has been made alkaline is crystallized using ligroin. Yield: 4.3 g (39% of theory), Melting point: 63°–65° C. Elemental analysis: $C_{12}H_{21}N_3O$ (223.32) calculated: C 64.5 H 9.5 N 18.8 O 7.2 found: C 64.0 H 9.4 N 18.5 O 8.0

EXAMPLE 21

N-(2-(2,5-Dimethyl-1-pyrrolyl)ethyl)-N-Boc-L-thiazolidine-4-carboxamide 11.6 g (0.05 mol) of N-Boc-L-thiazolidine-4-carboxylic acid and 8.1 g (0.05 mol) of carbonyldiimidazole in 10 ml of anhydrous DMF are stirred at 60° C. for 10 minutes. After addition of 6.9 g (0.05 mol) of 1-(-aminoethyl)2,5-dimetylpyrrole, dissolved in 10 ml of DMF, to the mixture it is stirred for 3 h, water is added, and the mixture is extracted with methylene chloride. The extract is chromatographed over a silica gel column (mobile phase: methylene chloride/ethyl acetate 1:1) and crystallized using dibutyl ether. Yield: 12.0 g (68% of theory), Melting point: 119°–121° C. Elemental analysis: $C_{17}H_{27}N_3O_3S$ (353.49) calculated: C 57.8 H 7.7 N 11.9 O 13.6 S 9.1 found: C 58.2 H 7.3 N 12.3 O 13.7 S 9.2 (Boc=tert.-butoxycarbonyl)

In analogy to the examples given, it is also possible to prepare, for example, the following compounds according to the invention:
(a) N-(2-(2,5-Dimethyl-1-pyrrolyl)ethyl)-L-thiazolidine-4-carboxamide
(b) 2,5-Dimethyl-1-(2-formylaminoethyl)pyrrole
(c) 2,5-Dimethyl-1-(2-propionylaminoethyl)pyrrole
(d) 2,5-Dimethyl-1-(3-acetylaminopropyl)pyrrole, melting point: 66°–67° C.
(e) 2,5-Dimethyl-1-(3-formylaminopropyl)pyrrole
(f) 2,5-Dimethyl-1-(3-propionylaminopropyl)pyrrole Pharmaceutical products are described in the examples which follow:

Example A

Emulsions containing 3 mg of active compound per 5 ml can be prepared using the following formulation:

| | |
|---|---|
| Active compound | 0.06 g |
| Neutral oil | q.s. |
| Sodium carboxymethylcellulose | 0.6 g |
| Polyoxyethylene stearate | q.s. |
| Pure glycerol | 0.2 to 2 g |
| Aromatizing substance | q.s. |
| Water (demineralized or distilled) | ad 100 ml |

Example B

Coated tablets containing an active compound according to the invention and another therapeutically active compound:

| | |
|---|---|
| Active compound | 6 mg |
| Propranolol | 40 mg |
| Lactose | 90 mg |
| Maize starch | 90 mg |
| sec. Calcium phosphate | 34 mg |
| Soluble starch | 3 mg |
| Magnesium stearate | 3 mg |
| Colloidal silica | 4 mg |
| | 270 mg |

Example C

Coated tablets containing an active compound according to the invention and another therapeutically active compound:

| | |
|---|---|
| Active compound | 5 mg |
| Molsidomine | 5 mg |
| Lactose | 60 mg |
| Maize starch | 90 mg |
| sec. Calcium phosphate | 30 mg |
| Soluble starch | 3 mg |
| Magnesium stearate | 3 mg |
| Colloidal silica | 4 mg |
| | 200 mg |

Example D

Capsules containing an active compound according to the invention and another therapeutically active compound:

| | |
|---|---|
| Active compound | 5 mg |
| Prazosine | 5 mg |
| Maize starch | 185 mg |
| | 195 mg |

Example E

Tablets can be prepared by the following formulation:

| | |
|---|---|
| Active compound | 2 mg |
| Lactose | 60 mg |
| Maize starch | 30 mg |
| Soluble starch | 4 mg |
| Magnesium stearate | 4 mg |
| | 100 mg |

Example F

The following composition is suitable for the preparation of soft gelatin capsules containing 5 mg of active compound per capsule:

| | |
|---|---|
| Active compound | 5 mg |
| Mixture of triglycerides of coconut oil | 150 mg |
| Capsule contents | 155 mg |

Example G

The following formulation is suitable for the preparation of coated tablets:

| | |
|---|---|
| Active compound | 1 mg |
| Maize starch | 100 mg |
| Lactose | 60 mg |
| sec. Calcium phosphate | 30 mg |
| Soluble starch | 3 mg |
| Magnesium stearate | 2 mg |
| Colloidal silica | 4 mg |
| | 200 mg |

Example H

Injection solutions containing 1 mg of active compound per ml can be prepared by the following formulation:

| | |
|---|---|
| Active compound | 1.0 mg |
| Polyethylene glycol 400 | 0.3 mg |
| Sodium chloride | 2.7 mg |
| Water for injections, to | 1 ml |

The following results, for example, were obtained during pharmacological testing. 1. "Nitrite hypoxia"

In this test, cerebral hypoxia is produced in mice with NaNO$_2$ (250 mg/kg subcutaneously) in accordance with the method of Gibson and Blass (J. Neurochem. 27, 37 (1976)), this hypoxia ending with the death of the experimental animals. It is ascertained whether the survival time is influenced by premedication with the test substance. The compounds of the invention are administered in a dose of 100 mg/kg p.o. The results are shown in the following Table. In this test, administering the known compound piracetam (=1-(aminocarbonylmethyl)pyrolidin-2-one) in a dose of 125 mg/kg p.o results in a percentage increase in the survival time of 15%.

TABLE

Percentage increase in the survival time on administeration of 250 mg/kg of NaNO$_2$ subcutaneously and premedication with compounds of the formula I

| Compound according to example No. | Percentage Increase |
|---|---|
| 5 | 41 |
| 13 | 20 |
| 14 | 20 |
| 1 | 10 |
| 11 | 14 |
| 3 | 23 |
| 12 | 27 |
| 2 | 12 |
| 21d | 29 |
| Piracetam (Comparison) | 15 |

2. "Passive avoidance"

The test apparatus is a light/dark box with an electrifiable grid floor in the dark part.

90 minutes after administration of the control injection and product injection, unexperienced male mice are treated with scopolamine hydrobromide (3 mg/kg subcutaneously). 5 minutes later, the mice are placed in the light part of the box. After being transferred to the dark part of the box, they receive an unpleasant electric shock in the feet. After 24 hours, each mouse is placed once in the light part of the test apparatus and the residence time (maximum of 180 seconds) is measured. The animals tested with an active dose of a product and scopolamine have a long residence time, as do the animals which have not been treated with scopolamine, whilst those treated with a control injection and scopolamine show a short residence time. The compounds of the invention are administered in a dose of 3 to 30 mg/kg p.o. The results are given in the following Table. In this test the known compound piracetam, administered in a dose of 60 mg/kg p.o., achieves a percentage decrease of 100%.

TABLE

Percentage decrease in scopolamine-induced amnesia, recognisable by an increase in the time until the animal enters the dark part of the passive avoidance test chamber.

| Compound according to Example No. | Dose (mg/kg) p.o. | Percentage Decrease |
|---|---|---|
| 5 | 3 | 108 |
| 21d | 30 | 42 |
| 13 | 30 | 36 |
| 14 | 30 | 70 |
| 12 | 30 | 75 |
| 15 | 30 | 111 |
| 19 | 30 | 90 |
| 18 | 3 | 124 |
| 20 | 30 | 108 |
| 2 | 30 | 121 |
| 21 | 30 | 79 |
| Piracetam (Comparison) | 60 | 100 |

We claim:

1. 2,5-Dimethylpyrrole of the formula I

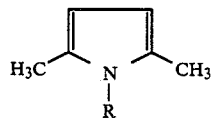

in which R denotes alkyl having 1 to 3 C atoms, which is substituted by acylamino of the formula —NH—CX—R$^1$; X represents an oxygen or sulphur atom, and R$^1$ is a radical selected from the group consisting of hydrogen; alkyl which has 1 to 5 C atoms; alkyl which has 1 to 5 C atoms and is substituted by -NH$_2$, monoalkylamino having 1 to 4 C atoms, dialkylamino having a total of 2 to 6 C atoms, alkoxy having 1 to 4 C atoms, phenoxy, or by phenoxy which in turn carries up to three substituents in the nucleus, namely an amino group, monoalkylamino having 1 to 4 C atoms, dialkylamino having a total of 2 to 6 C atoms, alkanoylamino having 1 to 6 C atoms, alkyl having 1 to 4 C atoms, alkoxy having 1 to 4 C atoms, fluorine, chlorine, bromine, hydroxyl, nitro, cyano, carboxyl or alkoxycarbonyl having 1 to 4 C atoms in the alkoxy group, as an optional second substituent of the nucleus one of the alkyl or alkoxy groups defined above or one of the above mentioned halogens and, as optional third substituent, one of the alkyl or alkoxy groups above; phenyl, phenyl which is substituted like the phenoxy radical mentioned above and their pharmacologically acceptable acid addition salts.

2. 2,5-Dimethyl-1-(2-acetylaminoethyl) pyrole.

3. A pharmaceutical formulation which exhibits encephalotropic and psychotropic effects when administered to a host having a disorder of brain function, having as active compound from about 0.5 to 90% by weight of a compound of claim 1, together with a pharmaceutically-acceptable vehicle and, optionally, a pharmaceutically-acceptable additive.

4. A method for treating disorders of brain function to produce encaphalotropic and psychotropic effects, which comprises administering an effective amount of a pharmaceutical formulation of claim 3, to a host afflicted with such a disorder.

* * * * *

UNITED STATES PATENT AND TRADEMARK OFFICE
CERTIFICATE OF CORRECTION

PATENT NO. : 4,837,225

DATED : June 6, 1989

INVENTOR(S) : Gerhard Zoller et al.

It is certified that error appears in the above-identified patent and that said Letters Patent is hereby corrected as shown below:

Col. 1, line 35, replace "2,3" with --2,5--; Col. 1, line 36, replace "a" with --as--; Col. 1, line 37, replace "dimehtyl" with --dimethyl--;

Col. 2, line 11, replace "carbocyl" with --carboxyl--; Col. 2, line 49, replace "theipine" with --thiepine--;

Col. 3, line 60, after "3-" insert --ylcarbonylamino,--;

Col. 4, line 36, replace "desried" with --desired--; Col. 4, line 38, replace "also be" with --also to--; Col. 4, line 64, replace "chloide" with --chloride--;

Col. 6, line 3, replace "9182" with --1982--; Col. 6, line 13, replace "2,3" with --2,5--; Col. 6, line 58, replace "sychotropic" with --psychotropic--; Col. 6, line 59, replace "disorder" with --disorders--;

Col. 7, line 13, replace "65" with --$\gamma$--; Col. 7, line 17, replace "exit" with --exist--; Col. 7, line 28, replace "enternal" with --enteral--;

UNITED STATES PATENT AND TRADEMARK OFFICE
CERTIFICATE OF CORRECTION

PATENT NO. : 4,837,225

DATED : June 6, 1989

INVENTOR(S) : Gerhard Zoller et al.

It is certified that error appears in the above-identified patent and that said Letters Patent is hereby corrected as shown below:

Col. 8, lines 34-35, replace "Pharmaceutircal" with --Pharmaceutical--; col. 8, line 53, replace "8.11" with --8.1--; Col. 8, line 68, replace ") 8.3" with --O 8.3--;

Col. 9, line 3, replace "pyrolidinyl" with --pyrrolidinyl--; Col. 9, line 5, replace "aminomethylpyrrolidine" with --aminomethylpyrrolidine--; Col. 9, line 22, replace "(188.8)" with --(188.28)--; Col. 9, line 41, replace "180" with --280--; Col. 9, line 49, replace "ehtyl" with --ethyl--; Col. 9, line 52, replace "(0.05 mol) of 1," --(0.04 mol) of 1--;

Col. 10, line 28, replace "pyrolyl" with --pyrrolyl--; Col. 10, line 44, replace "tetrahydrofura" with --tetrahydrofuran--; Col. 10, line 53, replace "CL" with --Cl--; Col. 10, line 54, replace "6.5" with --6.4--; Col. 10, line 58, replace "pyrolyl" with --pyrrolyl--;

Col. 11, line 17, replace "69%" with --68%--; Col. 11, line 19, replace "$C_{16}H_{19}CLN_2O_2$" with --$C_{16}H_{19}ClN_2O_2$--; same line, replace "CL" with --Cl--; Col. 11, line 20, replace "CL" with --Cl--; Col. 11, line 31, replace "reactionmixture" with --reaction mixture--; Col. 11, line 33, replace "acified" with --acidified--; Col. 11, line 36, replace "dibuyl" with --dibutyl--;

UNITED STATES PATENT AND TRADEMARK OFFICE
CERTIFICATE OF CORRECTION

PATENT NO. : 4,837,225

DATED     : June 6, 1989

INVENTOR(S) : Gerhard Zoller et al.

It is certified that error appears in the above-identified patent and that said Letters Patent is hereby corrected as shown below:

Col. 12, line 29, replace "2,3" with --2,5--; Col. 12, line 43, replace "cholorbenzoyl" with --chlorobenzoyl--; Col. 12, line 52, replace "Ligoin" with --ligroin--; same line, replace "thory" with --theory--;

Col. 13, lines 15-16, replace "1-(-amino-ethyl)2,5-dimetylpyrrole" with --1-(2-amino-ethyl)-2,5 dimethylpyrrole--;

In the claims:

Claim 2, replace "pyrole" with --pyrrole--.

Signed and Sealed this

Twenty-second Day of October, 1991

Attest:

HARRY F. MANBECK, JR.

*Attesting Officer*  *Commissioner of Patents and Trademarks*